United States Patent

Bunyan

[11] Patent Number: 5,935,111
[45] Date of Patent: Aug. 10, 1999

[54] APPLICATOR

[75] Inventor: Glen Walter Bunyan, Somersby, Australia

[73] Assignee: N.J. Phillips Pty. Limited, New South Wales, Australia

[21] Appl. No.: 08/852,559

[22] Filed: May 7, 1997

[30] Foreign Application Priority Data

May 8, 1996 [AU] Australia ................... PN9734

[51] Int. Cl.⁶ .......................... A61M 5/00; A61M 5/178
[52] U.S. Cl. .............................. 604/191; 604/183
[58] Field of Search .................. 604/68, 71, 91, 604/180, 183, 184, 187, 191, 214, 218; 222/135, 137, 386, 478; 239/528

[56] References Cited

U.S. PATENT DOCUMENTS

| | | | |
|---|---|---|---|
| 3,122,138 | 2/1964 | Geary | 128/215 |
| 4,403,989 | 9/1983 | Christensen | 604/137 |
| 4,487,602 | 12/1984 | Christensen | 604/137 |
| 4,673,395 | 6/1987 | Phillips | 604/191 |
| 5,593,388 | 1/1997 | Phillips | 604/135 |

FOREIGN PATENT DOCUMENTS 228209  3/1991  New Zealand.

Primary Examiner—Corrine McDermott
Assistant Examiner—Michael J. Hayes
Attorney, Agent, or Firm—Ladas & Parry

[57] ABSTRACT

An applicator (10) to deliver a medication from a first interacting cylinder (15) and piston (16) and a marking dye from a second interacting cylinder (20) and piston (21). Extending from the second piston (21) is a piston rod (23) which is engaged by the second piston (16) so as to be moved thereby.

12 Claims, 3 Drawing Sheets

APPLICATOR

TECHNICAL FIELD

The present invention relates to applicators to deliver medication to animals.

BACKGROUND OF THE INVENTION

Described in U.S. Pat. No. 4,673,395 is a dual barrel injector. The injector has two cylinders and pistons cooperating therewith, with the cylinders leading to a common outlet extending to a delivery nozzle or needle. The two cylinders receive separate liquids, which liquids are mixed prior to injection.

The above dual barrel injector does not permit the separate delivery of the liquids in instances where it is desirable to maintain the liquids separate.

OBJECT OF THE INVENTION

It is the object of the present invention to overcome or substantially ameliorate the above disadvantages.

SUMMARY OF THE INVENTION

There is disclosed herein an applicator comprising:

a body;

a first delivery member movably mounted on the body and operable to deliver a first medication;

an interacting piston and cylinder mounted on the body and enclosing a variable volume space;

first duct means to deliver a liquid to said space, second duct means through which liquid passes from said space to be ejected; and wherein said first delivery member and said interacting piston and cylinder are operatively associated so that actuation of said first delivery member reduces the volume of said space to cause delivery of said liquid.

BRIEF DESCRIPTION OF THE DRAWINGS

A preferred form of the present invention will now be described by way of example with reference to the accompanying drawings wherein.

DETAILED DESCRIPTION OF THE PREFERRED EMBODIMENT

Figure 1:
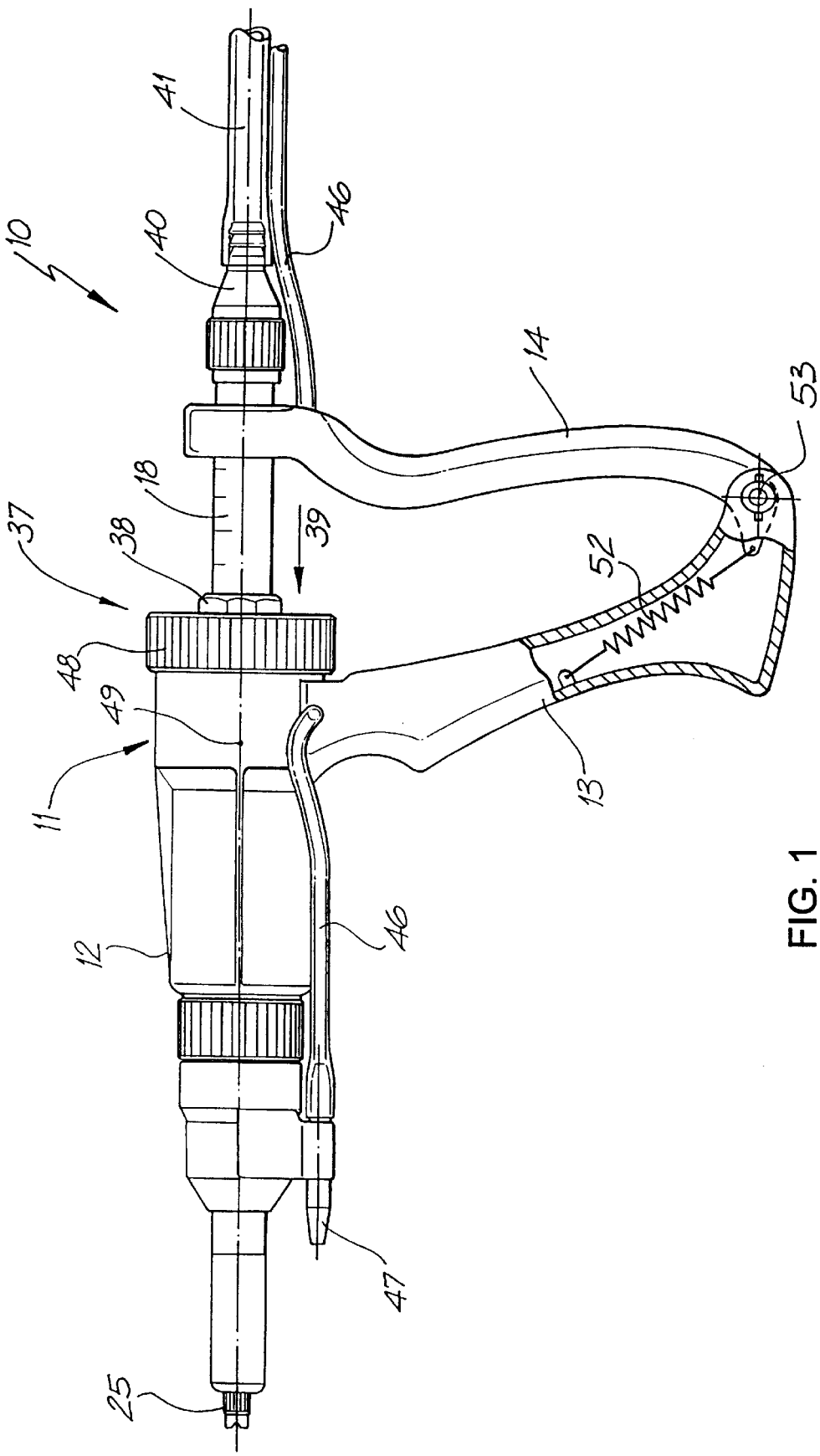
FIG. 1 is a schematic side elevation of an applicator.
Figure 2:
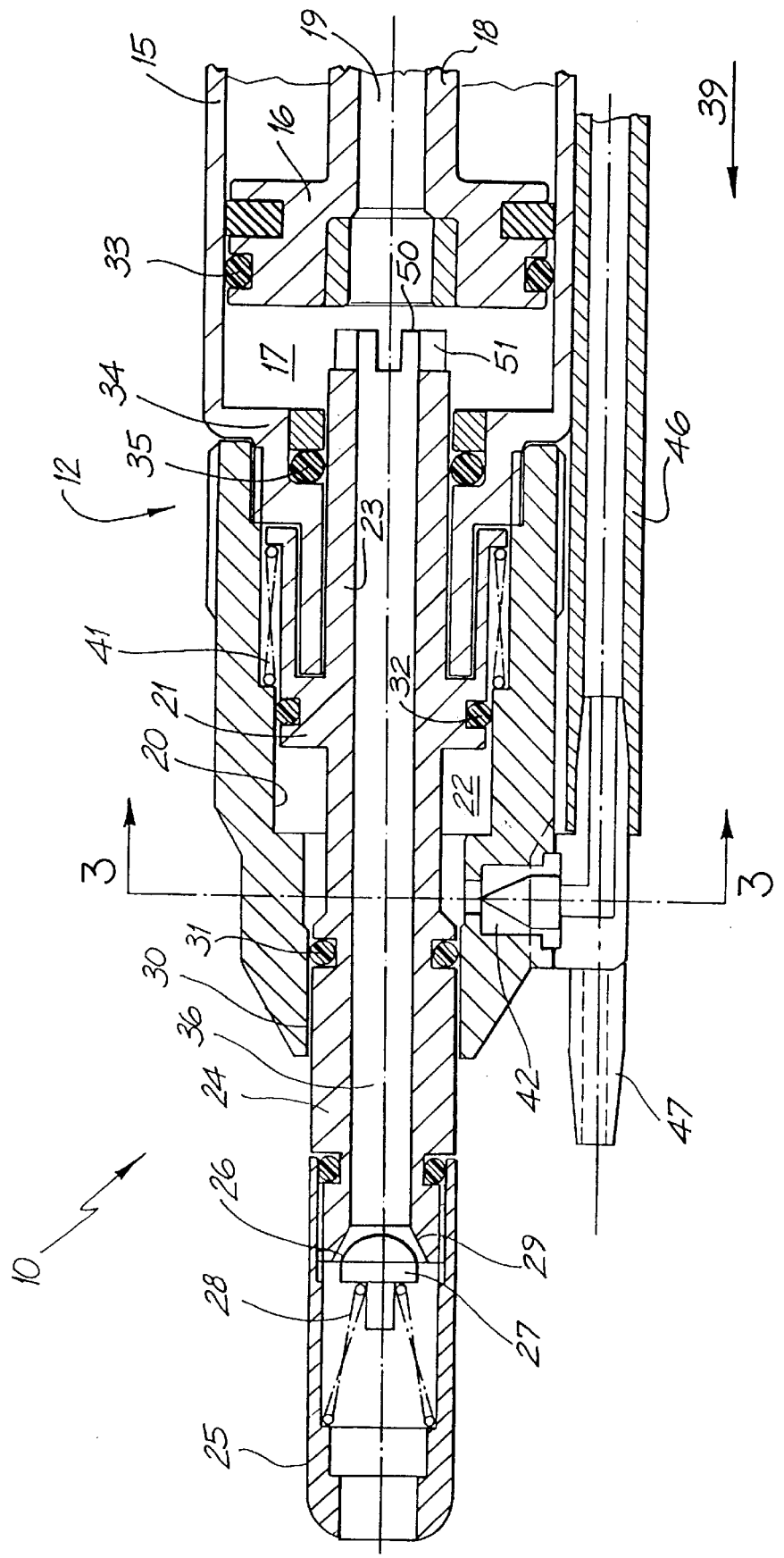
FIG. 2 is a schematic section side elevation of a portion of the applicator of FIG. 1.
Figure 3:
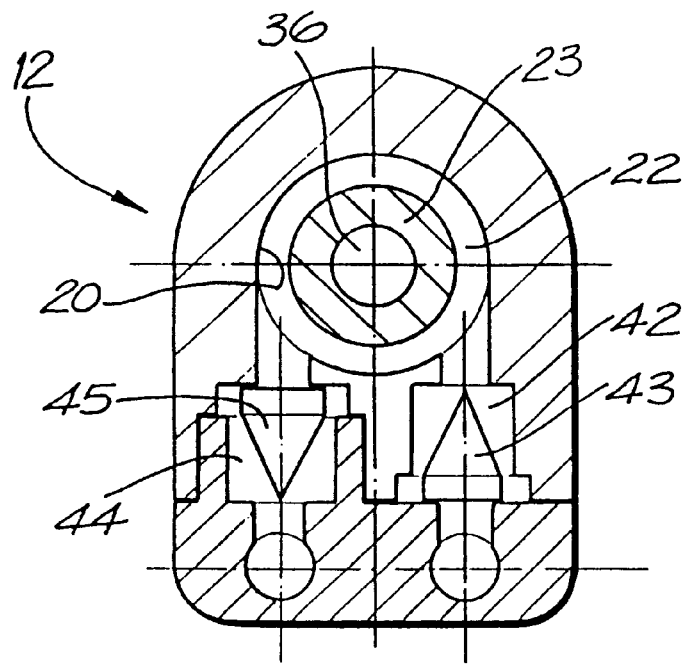
FIG. 3 is a schematic section end elevation of the applicator as illustrated in FIG. 2 sectioned along the line A—A.
Figure 4:
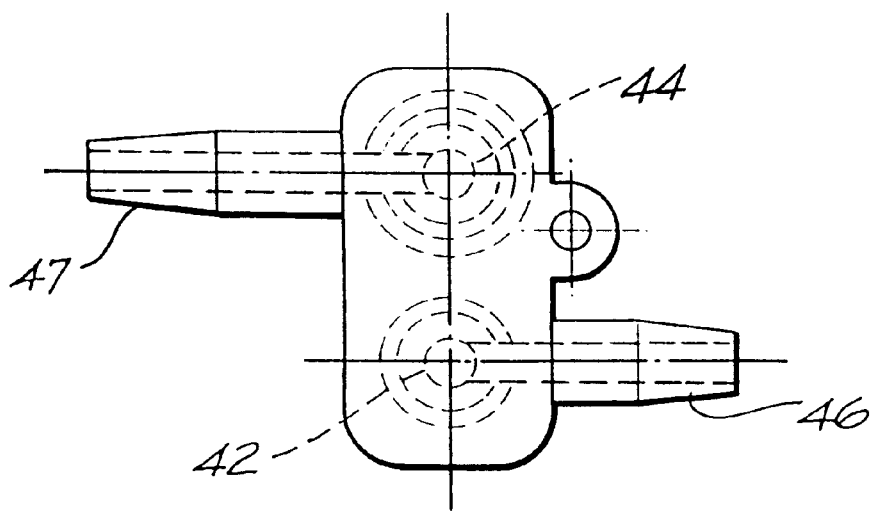
FIG. 4 is a schematic bottom plan view of a portion of the applicator as illustrated in FIG. 2.

In the accompanying drawings there is schematically depicted an applicator 10. The applicator 10 is adapted to deliver two liquids. For example, the first liquid could be a medication to be delivered to an animal. The medication could be a "pour on" treatment. The second liquid may be a further medication or in this particular example is a marking dye which is delivered to the animal to indicate that the animal has received the medication.

The applicator 10 includes a body 11 consisting of a base 12 from which there extends a handle 13. Typically attached to the tower end of tile handle 13 is a trigger 14, by means of a pivot pin 53. In operation, a user of the device grasps the applicator 10 so that the handle 13 and a trigger 14 are located in the palm of the hand. Movement of the trigger 14 towards the handle 13 causes actuation of the applicator 10.

The base 12 includes a first cylinder 15 cooperating with a piston 16 to close a variable volume first space 17, Extending from the piston 16 is a piston rod 18, through which there extends a central passage 19. The passage 19 extends to the space 17.

The body 12 provides a second cylinder 20 which cooperates with a second piston 21 to generally enclose a second variable volume space 22. Extending from the piston 21 is a piston rod 23 which projects into the space 17 so as to be engaged by the piston 16. Extending in the opposite direction to the rod 23 is a delivery member 24 extending to, in this embodiment, a delivery nozzle 25. Mounted within the delivery nozzle 25 is a one way valve assembly 26 including a movable valve member 27 engaged by a valve spring 28. The valve member 27 cooperates with a valve seat 29. The valve 26 ensures that liquid is not drawn back into the applicator 10.

The delivery member 24 passes through a passage 30 in the base 12 and sealingly engages the body 12 by means of a seal 31. The seal 31 permits sliding movement between the delivery member 24 and base 12.

The piston 21 slidably engages the cylinder 20 by means of a seal 32 while the piston 16 engages a cylinder 15 by means of a seal 33. The cylinder 15 has a portion 34 of reduced size, which portion 34 supports a seal 35 to slidably engage the external surface of the rod 23.

Extending longitudinally through the rod 23 and member 24 is a passage 36.

The piston rod 18 extends rearwardly through a dose adjustment mechanism 37, which in this embodiment is an adjustment member 38 which threadably engages the rod 18 so as to be movable therealong. Upon rotation of the member 38 about the longitudinal axis of the rod 18. The rod 18 passes through a yoke mechanism in the top of the trigger 14 so that upon movement of the trigger 14 toward the handle 13, the rod 18 is caused to move in the direction of the arrow 39. The extremity of the rod 18 is provided with an adaptor 40 which couples the rod 18 to a flexible conduit 41 extending to a reservoir. Located in the adaptor 40 is a one way valve mechanism similar to the valve 26 so that fluid will only pass through the valve mechanism in the direction of the arrow 39.

A spring 52 extends between the handle 13 and trigger 14 so as to bias the trigger 14 to pivot away from the handle 13 and therefore move the piston 16 so that the space 17 has its maximum volume, which maximum volume is determined by the mechanism 37.

Extending between the base 12 and the piston 21 is a spring 41 to cause the piston 21 to move in a direction to maximise the volume of the space 22.

The space 22 is provided with an inlet duct 42 including a one way valve 43 to restrict fluid being delivered in a direction toward the space 22, and an outlet duct 44 including a one way valve 45 restricting fluid to flow therethrough only in a direction leaving the space 22. The duct 42 is attached to a conduit 46 which passes through the handle 13 and trigger 14 and extends therefrom to a further reservoir containing liquid to be delivered via the nozzle 47 communicating with the outlet duct 44.

The dose adjustment mechanism 37 includes a does adjustor 48 which is rotatably mounted on the base 12 so as to be rotatable about the longitudinal axis 49 of the push rod 18. The dose adjustor 48 has a hexagonal central aperture through which the member 38 slides, with the member 38 having a complimentary shape and engaged with the hexagonal aperture of the adjustor 48. The member 38 is slidable through the adjustor 48 but is threadably engaged with the rod 18. With rotation of the adjustor 48 about the rod 18, the member 38 moves longitudinally of the rod 18. Its position along the rod 18 determines the travel of the piston 16 and therefore the size of the dose delivered through the nozzle 25.

In operation of the above described applicator 10, the two pistons 16 and 21 are urged to move in the opposite direction to the arrow 39 by the spring 41 and the spring 52 described with reference to the handle 13 and trigger 14. At this time a first liquid is contained in the space 17, and a second liquid is contained in the space 22. When the operator squeezes the trigger 14 so as to rove it towards the handle 14, the piston rod 18 by movement of the piston 16 reduces the volume of the space 17. Liquid is then moved down the passage 36 and leaves the applicator 10 via the nozzle 25. The amount of liquid so ejected is determined by the position of the member 38 along the rod 18. The member 38 ultimately abuts a surface of the body 11 limiting the stroke of the piston 16. As the piston 16 travels in the direction of the arrow 39, it eventually engages the end of the rod 23. This then causes movement of the piston 21 to reduce the volume of the space 22. The liquid in the space 22 is then ejected via the nozzle 47. Movement of the piston 21 ceases when movement of the piston 16 ceases. More particularly, the piston 16 engages end portions 50 of the rod 23. The end portions 50 are spaced by apertures 51 so that fluid can still leave the space 17 and enter the passage 36.

When the trigger 14 is released both pistons 16 and 21 move in the opposite direction to the arrow 39 under the influence of the spring 41 and the spring 52 contained in the handle 13 and trigger engaging 14. The first liquid is then drawn into the space 17 and the second liquid drawn into the space 22.

In the above described preferred embodiment the first liquid which passes through the space 17 is a medication while the liquid that passes through the space 22 is a marking dye. However, in that regard it should be appreciated that the liquid that passes through the space 22 may be a further medication. In a modification of this device the piston 17 and its associated cylinder 15 may be eliminated and the rod 23 and member 24 used to eject a pellet from a magazine. In a still further embodiment the rod 23 and the member 24 may be used to deliver a bolii.

I claim:

1. An applicator 10 comprising:

a body 11;

a delivery member 24 movably mounted on the body 11 and operable to deliver a medication;

an interacting piston 21 and cylinder 20 mounted on the body 11 and enclosing a variable volume space 22;

first duct means 42 to deliver a liquid to said space 22;

second duct means 44 through which liquid passes from said space 22 to be ejected; and wherein said delivery member 24 and said interacting piston 21 and cylinder 20 are operatively associated so that actuation of said delivery member 24 to deliver said medication reduces the volume of said space 22 to cause delivery of said liquid separately with respect to said medication.

2. The applicator 10 of claim 1 wherein:

said cylinder 20 is fixed to said body 11 and said piston 21 is movable relative thereto between a first position at which said space 22 has a maximum volume and a second position at which said space 22 is reduced in volume; and said delivery member 24 is fixed to said piston 21 so as to move therewith.

3. The applicator 10 of claim 1 wherein:

said piston 21 and cylinder 20 are a first piston 21 and cylinder 20 and said applicator 10 further includes a second interacting piston 16 and cylinder 15 enclosing a variable volume space 17 for containing a liquid providing said medication; and said delivery member 24 includes a delivery passage 36 extending to the space 17 of the said second piston 16 and cylinder 15 so that the liquid providing said medication is delivered through said passage 36 as the space 17 of said second piston 16 and cylinder 15 is reduced.

4. The applicator 10 of claim 3 wherein:

said second cylinder 15 is fixed to said body 11 and said second piston 16 moves relative thereto between a first position at which the volume of the space 17 of said second piston 16 and cylinder 15 is a maximum and a second position at which the volume of the space 17 of said first piston 21 and cylinder 20 is reduced.

5. The applicator 10 of claim 4 wherein said second piston 16 causes movement of said first piston 21 when said second piston 16 is displaced from its first position.

6. The applicator 10 of claim 5 further including:

extension means 23 extending from said first piston 21 and into the space 17 of said second piston 16 and cylinder 15, said extension means 23 being engaged by said second piston 16 to cause movement of said first piston 21, with said extension means 23 having a passage 36 communicating with the passage 36 of said delivery member 24 and communicating with the space 17 of said second piston 16 and cylinder 15 so that liquid contained in the space 17 of said second piston 16 and cylinder 15 passes through said 40 extension means 23 to be delivered to said delivery member 24.

7. The applicator 10 of claim 6 further including:

a piston rod 18 extending from said second piston 16; and a passage 19 extending through said piston rod 18 enabling the delivery of liquid to the space 17 of said second piston 16 and cylinder 15.

8. The applicator 10 of claim 7 further including a handle 13 fixed to said body 11 and a trigger 14 pivotally mounted on said handle 13 and associated with said piston rod 18 so that movement of said trigger 14 towards said handle 13 causes movement of said piston rod 18 to reduce the volume of the space 17 of said second piston 16 and cylinder 15 and the subsequent reduction of the volume of the space 22 of said first piston 21 and cylinder 20.

9. The applicator 10 of claim 8, further including spring means urging the pistons 16,21 and cylinders 15,20 to move to a position at which the volumes of the spaces 17,22 are at a maximum.

10. The applicator 10 of claim 9, further including adjustment means 48 to vary the maximum volume of the space 17 of said second piston 16 and cylinder 15.

11. The applicator 10 of claim 1 comprising first nozzle means 47 operatively associated with the space 22 for providing a separate passage through which the separately delivered liquid is ejected.

12. The applicator 10 of claim 11 comprising second nozzle means 25 operatively associated with delivery member 24 for providing a passage through which the medication is ejected.

* * * * *